(12) United States Patent
Strother et al.

(10) Patent No.: US 8,700,177 B2
(45) Date of Patent: Apr. 15, 2014

(54) SYSTEMS AND METHODS FOR PROVIDING PERCUTANEOUS ELECTRICAL STIMULATION

(75) Inventors: Robert B Strother, Willoughby Hills, OH (US); Jonathan L Sakai, Fairview Park, OH (US); Joseph W Boggs, II, Carrboro, NC (US); Kathryn W Stager, University Heights, OH (US); Maria E Bennett, Beachwood, OH (US); Stuart Rubin, Orange Village, OH (US)

(73) Assignee: NDI Medical, LLC, Cleveland, OH (US)

( * ) Notice: Subject to any disclaimer, the term of this patent is extended or adjusted under 35 U.S.C. 154(b) by 0 days.

(21) Appl. No.: 13/440,784

(22) Filed: Apr. 5, 2012

(65) Prior Publication Data

US 2013/0096641 A1    Apr. 18, 2013

Related U.S. Application Data

(63) Continuation-in-part of application No. 12/462,384, filed on Aug. 3, 2009, which is a continuation-in-part of application No. 12/653,029, filed on Dec. 7, 2009, and a continuation-in-part of application No. 12/653,023, filed on Dec. 7, 2009, which is a continuation-in-part of application No. 13/323,152, filed on Dec. 12, 2011, now abandoned, which is a continuation of application No. 13/095,616, filed on Apr. 27, 2011, now abandoned.

(60) Provisional application No. 61/472,063, filed on Apr. 5, 2011, provisional application No. 61/137,652, filed on Aug. 1, 2008, provisional application No. 61/201,030, filed on Dec. 5, 2008, provisional application No. 61/343,325, filed on Apr. 27, 2010.

(51) Int. Cl.
*A61N 1/04*    (2006.01)

(52) U.S. Cl.
USPC ............................................. 607/115

(58) Field of Classification Search
USPC ..................... 607/2, 115, 149–152
See application file for complete search history.

(56) References Cited

U.S. PATENT DOCUMENTS

2008/0065182 A1*  3/2008  Strother et al. .............. 607/115
2010/0042180 A1*  2/2010  Mueller et al. ................ 607/46

* cited by examiner

*Primary Examiner* — Brian T Gedeon
(74) *Attorney, Agent, or Firm* — McDonald Hopkins, LLC

(57) ABSTRACT

Systems and methods according to the present invention relate to a novel peripheral nerve stimulation system for the treatment of pain, such as pain that exists after amputation.

7 Claims, 10 Drawing Sheets

SYSTEMS AND METHODS FOR PROVIDING PERCUTANEOUS ELECTRICAL STIMULATION

RELATED APPLICATIONS

This application is a continuation-in-part of U.S. patent application Ser. No. 12/462,384, now U.S. Pat. No. 8,463,383, filed 3 Aug. 2009, and entitled "Portable Assemblies, Systems, and Methods for Providing Functional or Therapeutic Neurostimulation," which is incorporated herein by reference in its entirety and which claims the benefit of U.S. Provisional Patent Application Ser. No. 61/137,652, filed 1 Aug. 2008, and entitled "Portable Assemblies, Systems, and Methods for Providing Functional or Therapeutic Neurostimulation."

This application is also a continuation-in-part of U.S. patent application Ser. No. 12/653,029, filed 7 Dec. 2009, and entitled "Systems and Methods To Place One or More Leads in Tissue for Providing Functional and/or Therapeutic Stimulation," which is incorporated herein by reference in its entirety and which claims the benefit of U.S. Provisional Patent Application Ser. No. 61/201,030, filed 5 Dec. 2008, and entitled "Systems and Methods To Place One or More Leads in Tissue for Providing Functional and/or Therapeutic Stimulation."

This application is also a continuation-in-part of U.S. patent application Ser. No. 12/653,023, filed 7 Dec. 2009, and entitled "Systems and Methods To Place One or More Leads in Tissue to Electrically Stimulate Nerves of Passage to Treat Pain," which is incorporated herein by reference in its entirety and which claims the benefit of U.S. Provisional Patent Application Ser. No. 61/201,030, filed 5 Dec. 2000, and entitled "Systems and Methods To Place One or More Leads in Tissue for Providing Functional and/or Therapeutic Stimulation."

This application is also a continuation-in-part of U.S. patent application Ser. No. 13/323,152, now abandoned, filed 12 Dec. 2011, and entitled "Systems and Methods for Percutaneous Electrical Stimulation," which is a continuation of U.S. patent application Ser. No. 13/095,616, now abandoned, filed 27 Apr. 2011, and entitled "Systems and Methods for Percutaneous Electrical Stimulation," which is incorporated herein by reference in its entirety and which claims the benefit of U.S. Provisional Patent Application Ser. No. 61/343,325, filed 27 Apr. 2010, and entitled "Systems and Methods for Percutaneous Electrical Stimulation."

Every combination of the various embodiments contained in the incorporated reference applications may be formed so as to carry out the intention of embodiments of the invention described below.

BACKGROUND OF THE INVENTION

Approximately 185,000 individuals in the U.S. undergo an amputation each year. The majority of new amputations result from vascular disorders such as diabetes, with other causes including cancer and trauma. Almost all amputees (95%) have intense pain during the recovery period following their amputation, either sensed in the portion of the limb that remains (residual limb pain) or in the portion of the limb that has been removed (phantom pain). It is critical to treat this sub-chronic pain condition quickly and effectively to avoid the significant social, economic, and rehabilitation issues associated with severe post-amputation pain. Other types of neuropathic pain affect over 6 million Americans.

Almost all amputees (95%) have pain related to their amputation: approximately 68-76% of amputees have residual limb pain (RLP) and 72-85% of amputees have phantom limb pain (PLP). Their severity and prevalence make them significant medical problems. Pain can lead to discouragement, anger, depression, and general suffering. PLP and RLP frequently cause further disability and greatly reduce quality of life (QOL). In amputees with severe pain, it is frequently the pain rather than the loss of a limb that most impacts daily activities and employment. Amputee pain has a significant economic impact on the patient and society. For the patient, the median cost of medications exceeds $3,000/year and the median cost for a treatment regimen provided by a pain management center is over $6,000/year. The annual cost in the U.S. to manage post-amputation pain is estimated to be over $1.4 billion for medications and over $2.7 billion for pain center treatment programs. When the overall costs of pain management care are summed, the annual cost can exceed $30,000/patient for a cost of over $13 billion/year to treat amputees with severe pain in the US.

Present methods of treatment are unsatisfactory in reducing pain, have unwanted side effects, and are not suited for temporary use. Electrical stimulation of nerves can provide significant (>50%) pain relief, but present methods of implementation are either inappropriate for sub-chronic pain due to their invasiveness, or are uncomfortable and inconvenient to use. We have developed an innovative, minimally invasive method of delivering temporary electrical stimulation to target nerves. Preliminary data on treating amputee pain using methods according to the present invention are promising, but there is a significant need for a stimulation system that overcomes the technical and clinical barriers of presently available devices, including imprecise programming (requiring precise lead placement which is impractical for widespread use) and lack of moisture ingress protection (requiring removal of system during some daily activities).

PLP and RLP are severe and debilitating to a large proportion of amputees, who often progress through a series of treatments without finding relief. Most patients are managed with medications. Non-narcotic analgesics, such as non-steroidal anti-inflammatory drugs (NSAIDS), are commonly used but are rarely sufficient in managing moderate to severe pain. Trials of narcotics have failed to show significant reduction in PLP, and they carry the risk of addiction and side effects, such as nausea, confusion, vomiting, hallucinations, drowsiness, headache, agitation, and insomnia. Other medications such as antidepressants are used for neuropathic pain, but their use for post-amputation pain is based primarily on anecdotal evidence and there are few controlled clinical trials to support their efficacy for post-amputation pain. Physical treatments (e.g., acupuncture, massage, heating/cooling of the residual limb) have limited data to support their use and are not well accepted. Psychological strategies, such as biofeedback and psychotherapy, may be used as an adjunct to other therapies but are seldom sufficient on their own, and there are few studies demonstrating their efficacy. Mirror-box therapy has demonstrated mixed results and is not widely used. Few surgical procedures are successful and most are contraindicated for the majority of the amputee patients 11. Studies have shown that pain resolves over the first 6 months following amputation for some patients. Within 6 months, RLP resolves for 60% of patients and PLP resolves for 10% of patients, with another 40% experiencing a significant reduction in pain intensity, making it inappropriate to use invasive methods before establishing that the pain is long-term (>6 months).

Prior electrical stimulation has been attempted. Transcutaneous electrical nerve stimulation (TENS, i.e., surface stimulation) is a commercially available treatment and has been demonstrated at being at least partially successful in reducing post-amputation pain. However, TENS has a low (<25%) success rate due to low patient compliance. Patients are non-compliant because the stimulus intensity required to activate deep nerves from the skin surface can activate cutaneous pain fibers leading to discomfort, the electrodes must be placed by skilled personnel daily, and the cumbersome systems interferes with daily activities. Spinal cord stimulation (SCS), motor cortex stimulation, and deep brain stimulation (DBS) have evidence of efficacy, but their invasiveness, high cost, and risk of complications makes them inappropriate for patients who may only need a temporary therapy. High frequency nerve block has been shown to decrease transmission of pain signals in the laboratory, but the therapy has not been developed for clinical use. Historically, peripheral nerve stimulation (PNS) for pain has not been widely used due to the complicated approach of dissecting nerves in an open surgical procedure and placing leads directly in contact with these target nerves. Such procedures are time consuming and complex (greatly limiting clinical use outside of academic institutions), have risks of damaging nerves, and often (27%) have electrode migration or failure. Other groups are developing percutaneous electrode placement methods, but their methods still require delicate, placement and intimate contact with the nerve, making them prone to complications and migration (up to 43%) because the technology lacks sufficient anchoring systems, leading to loss of pain relief and rapid failure (averaging 1-2 revisions/patient).

SUMMARY OF THE INVENTION

A system according to the present invention relates to a novel, non-surgical, non-narcotic, minimally-invasive, peripheral nerve stimulation pain therapy intended to deliver up to 6 months or more of therapy to patients that may be experiencing pain, such as post-amputation pain. In one embodiment, system components are an external stimulator, preferably a 2-channel stimulator that connects to up to two percutaneous leads, a charging pad for recharging the stimulator, and wireless controllers used by the patient and the clinician.

Systems and methods according to the present invention overcome at least the limitations or drawbacks of conventional TENS systems, such as cutaneous pain and low compliance, thought to be at least partially due to the cumbersome nature of prior systems. Systems and methods according to the present invention also overcome at least some of the limitations or drawbacks of conventional surgical options such as SCS, DBS, and surgically-implemented PNS, such as invasiveness, cost, and risk of complications. Systems and methods according to the present invention relate to delivering stimulation percutaneously (electrical current traveling through a lead placed through the skin) which has significant advantages. Such stimulation may be provided using methods that are minimally invasive and reversible (making it ideal for treating temporary pain), easy for pain specialists to perform (due to its similarity to common procedures such as injections), and can be trialed without long-term commitment. In addition, the electrodes of the electrical leads only need to be placed within centimeters of the nerve, reducing the risk of nerve injury (as the electrode does not touch the nerve) and making the lead placement procedure simple for non-surgeons. Finally, improved percutaneous leads have a proven anchoring system, reducing susceptibility to electrode migration. At the conclusion of use, the lead is removed by gentle traction. Systems and methods according to the present invention may employ a percutaneous lead with a long history of successful use is multiple pain indications including amputee pain. Data suggest that systems and methods according to the present invention will have a low risk of complications. For instance, in a long-term study of 1713 leads placed in the lower extremities and trunk, there were 14 (0.9%) electrode fragment-associated tissue reactions that resolved when the fragments were removed with forceps, and 14 (0.9%) superficial infections that resolved when treated with antibiotics and/or the lead was removed.

Ongoing studies are being used to investigate the safety & efficacy of treating amputee pain using percutaneous leads connected to surface stimulators to deliver safe stimulation percutaneously, and the results are promising. Five subjects with amputations have received in-clinic (i.e., trial) therapy. Three subjects had amputations due to trauma, one due to cancer, and one due to vascular disease. The subjects had used various combinations of medications (narcotic and non-narcotic), physical therapy, injections, and nerve blocks in the past without success. Stimulation was delivered to the femoral nerve (n=1), the sciatic nerve (n=1), or both (n=3) depending on the location of pain. Of the three subjects who reported RLP at baseline, the average reduction in pain during in-clinic trial was 64%. The two subjects who reported PLP at baseline reported a 60% reduction in pain during the in-clinic testing. One subject did not report pain relief due to vascular dysfunction in the amputated limb. It was determined that the nerves would not respond to stimulation during the in-clinic testing and remove the lead through gentle traction. If this patient had received a trial stage system for SCS, the leads would have required open surgery for removal. The present approach allows for minimally-invasive screening of patients to determine responders. Thus far, three subjects have received the therapy at home for ≤2 weeks. All three subjects reported significant pain relief for the duration of therapy use. There have been no adverse events to date. Results are promising, but using prior available surface stimulators to deliver stimulation through percutaneous leads has significant limitations (e.g., per pulse charges that can be unsafe with percutaneous leads if not limited by a technical modification, lack of moisture ingress protection forcing subjects to remove the system when showering, burdensome cables that can snag), making it unfeasible to deliver therapy, under methods according to the present invention, using existing systems for a full 6-month period. Systems and methods according to the present invention address unfortunate shortcomings of prior systems, as they may be used to deliver optimal safe and effective percutaneous stimulation that will maximize clinical benefit.

Prior systems and methods fail to provide an effective and minimally invasive treatment option for patients with post-amputation pain, forcing many of them to suffer with severe pain during their initial recovery or resort to an invasive therapy that may not be necessary in the long-term. Systems and methods according to the present invention have the capability to provide a therapy that has the potential for a high rate of efficacy with minimal side effects, has a simple procedure performed in an outpatient setting, is temporary & reversible, and has established reimbursement coding and coverage policies (existing codes and coverage policies reimburse the therapy cost and make the procedure profitable for the hospital % physician). Systems and methods according to the present invention may be used to treat other types of neuropathic pain, such as complex regional pain syndrome (CRPS). CRPS is challenging to treat due to its poorly understood pathophysiology, and few patients receive pain relief from available treatments. PNS produces dramatic pain relief in most patients with CRPS, but existing methods require surgically placing the lead in intimate contact with the nerve.

These procedures are time consuming & complex (greatly limiting clinical use outside of academic institutions), have risks of nerve damage, and often (27%) have lead migration or failure. Another neuropathic pain that may be treated with systems and methods according to the present invention is post-herpetic neuralgia, which is severe but often temporary, making invasive surgeries inappropriate. Pain due to diabetic neuropathy, which is poorly controlled using medications, may also be treated using systems and methods according to the present invention. As indicated, over 6 million Americans suffer from neuropathic pain, resulting in a negative impact on quality of life (QOL) and profound economic costs. Systems and methods according to the present invention may change how neuropathic pain is managed by providing clinicians with a minimally-invasive, simple, reversible, and effective treatment option, resulting in a significant, decrease in the socioeconomic consequences of neuropathic pain and an improvement in the QOL of millions of Americans.

DESCRIPTION OF THE PREFERRED EMBODIMENT

Figure 1:
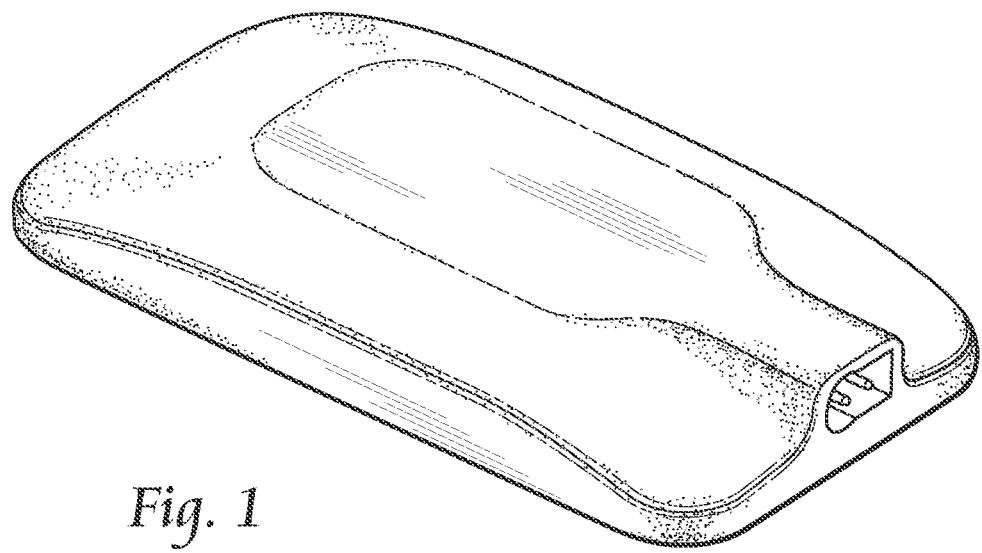
FIGS. 1-7 depict a preferred external stimulator according to the present invention.
Figure 2:
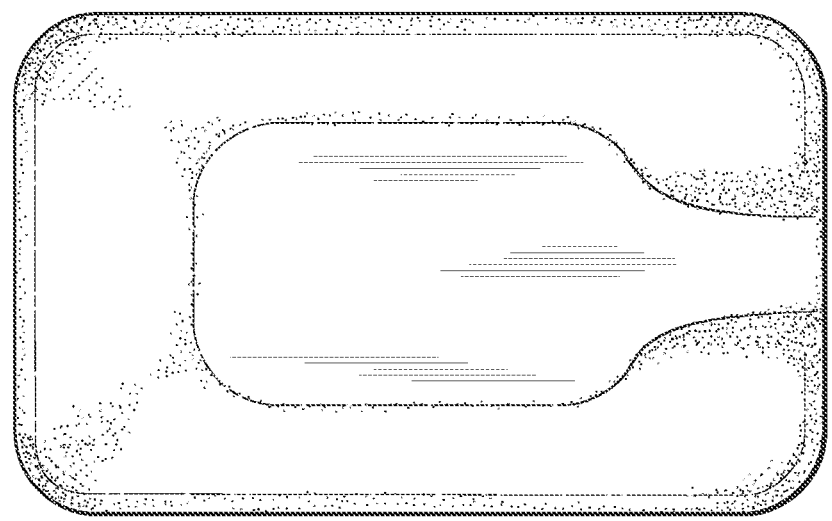
Figure 3:
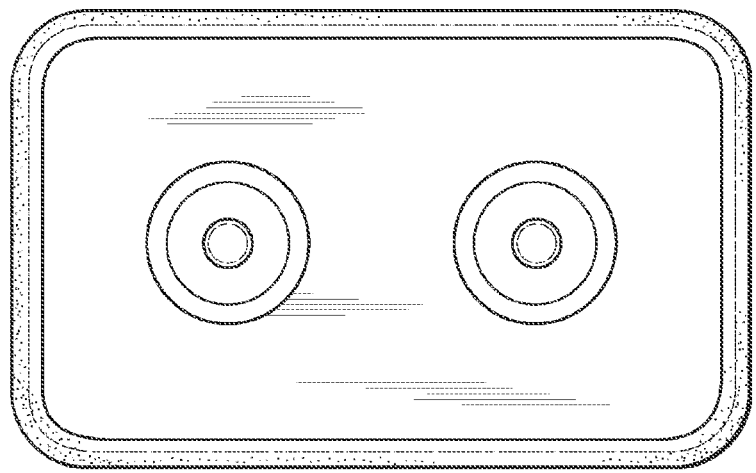
Figure 4:
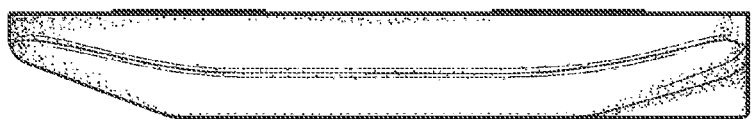
Figure 5:
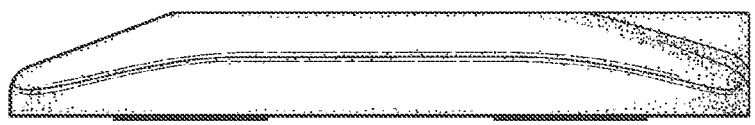
Figure 6:
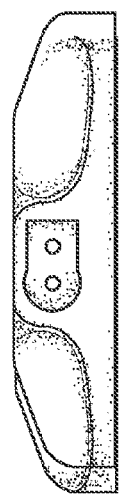
Figure 7:
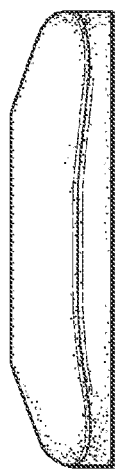
Figure 8:
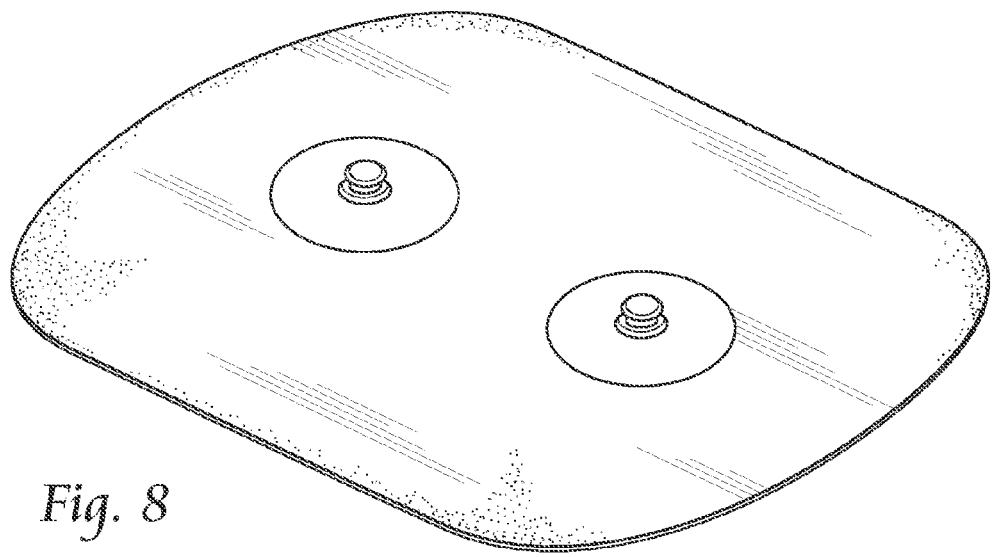
FIGS. 8-11 depict a preferred mounting patch according to the present invention.
Figure 9:
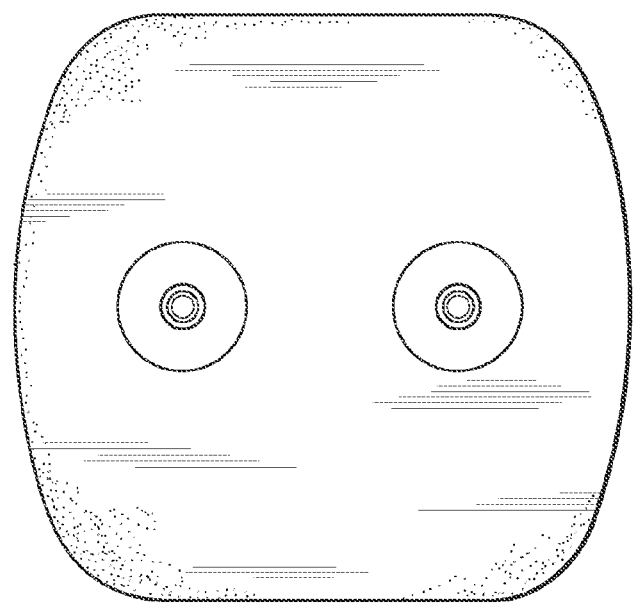
Figure 10:
Figure 11:

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

Systems, components, or methods according to the present invention may provide safety improvements, such as electrical safety improvements that may be provided by improved moisture ingress protection.

Systems, components, or methods according to the present invention may provide stimulation output improvements, such as direct-to-nerve stimulation and current-controlled output.

Systems, components, or methods according to the present invention may provide stimulation usability improvements, such as decreased physical size, wireless stimulation control, and decreased maintenance requirements.

A system according to the present invention may include one or more of the following components: an external stimulator, percutaneous leads, a patient controller, a charging pad, and a clinician controller. The external stimulator is a preferably small, lightweight pod that may be selectively mountable to a replaceable adhesive patch that may function as a return electrode. The external stimulator is preferably less than four centimeters wide, less than six centimeters long, and less than one centimeter thick. More preferably, the external stimulator is about 3.6 centimeters wide, about 5.8 centimeters long, and about 0.8 centimeters thick. The external stimulator weighs preferably less than 30 grams, and more preferably less than 24 grams. The external stimulator may include or not include a power source. If the external stimulator does not include a power source, electrical power is provided to electrical stimulation circuitry housed within the stimulator by a battery that is preferably provided in the adhesive patch. If the external stimulator does house a power source, the power source is preferably a battery that may be inductively recharged.

The external stimulator may be physically mounted to and supported by an adhesive patch that may be adhered to the skin spaced from, but preferably near (preferably less than fifteen centimeters) the exit site of the percutaneous leads (preferably proximal to a prosthetic limb, if used). The adhesive patch may provide a mounting location for the external stimulator, but may also function as a surface electrode for either stimulating, as an active electrode, or serving as a non-stimulating return electrode. Thus, the mounting mechanism between the patch and the external stimulator is preferably electrically conductive, such as one or more metallic snap structures that are mateable with corresponding seat structures provided on the external stimulator. The patch may provide an additional, alternate, and/or back-up power supply for electrical stimulation circuitry contained in the external stimulator. A preferred smooth and low profile design of the housing of the external stimulator, helps reduce a majority of common problems associated with existing external stimulators, including accidental button activation and snagging on clothes (which can disconnect or break the electrodes). Wireless control, such as with a remote controller, allows further miniaturization of the stimulator, decreasing the footprint of the device on the skin surface and allowing it to be worn almost imperceptibly under clothing, in contrast to commercially available stimulators which are typically worn outside of clothing due to their large size and the need to view the display screen. Using a system according to the present invention, a patient may utilize a controller, such as a key-fob like device, to adjust the intensity of each percutaneous stimulation channel within a safe and effective range. Recharging the power source of the stimulator may be performed in a variety of ways. If a power source is provided in the stimulator housing, the power source is preferably a battery that may be inductively recharged, preferably within 2 hours by placing it on a charging pad. A clinician controller may be provided in the form of a notepad computer with custom software and a wireless communications interface or adaptor for programming stimulus parameters in the external stimulator or the controller used by the patient, and reading patient compliance data from the external stimulator or from the controller used by the patient.

Systems according the present invention are preferably designed to meet preferred safety, output, and usability goals that are not met by presently available devices, see Table b.1, below. Safety features such as maximum per pulse charge safe for percutaneous stimulation, moisture ingress protection for safe use during daily activities including showering, and limited programming by patients, may be incorporated. Design mechanisms to deliver minimally-invasive and effective therapy, such as bypassing cutaneous pain fibers and current-controlled output, may also be included. Features that improve comfort and usability may also be incorporated, such as miniaturization and low maintenance.

TABLE B.1

Systems and methods according to the present invention address limitations of prior available devices.

|  |  | Possible limitations of available technology (surface stimulators and trial SCS stimulators) | Preferred features of embodiments of systems according to present invention |
|---|---|---|---|
| SAFETY | Output safe for stimulus delivery via percutaneous leads | Surface stimulators can be adjusted to per pulse charges that can damage tissue when used with percutaneous leads, which would be an off-label use | Full parameter range is safe for use with percutaneous leads (preferred maximum per pulse charge injection of $4 \, \mu C = 0.4 \, \mu C/mm^2$) |
|  | Moisture ingress protection suitable for wearing on the skin during all daily activities | Most surface stimulators rated as IPX0 (ordinary equipment). Must be removed during daily activities such as showering. | Rated as IP44 (protection from water sprayed from all directions). Remains safe and reliable despite perspiration, showering, etc. |
|  | Patient adjustment of stimulus intensity within a safe & effective range | Surface stimulators allow unrestricted adjustment, resulting in stimulus output that can be ineffective or unsafe | Allows patient to select from a safe and effective range of intensities with minimal clinician programming. |
|  | Minimally invasive lead placement | Trial SCS leads are placed via open procedures requiring imaging | percutaneous leads are placed through the skin by non-surgeons |
| OUTPUT | Comfortable therapy (for high compliance) | Surface stimulation can activate cutaneous pain fibers leading to discomfort/pain | Therapy is delivered directly to the nerves, bypassing cutaneous pain fibers. |
|  | Current-controlled output to minimize variability among patients | Many surface stimulators are voltage-controlled: the output current depends on surface electrode-to-tissue impedance which varies over time and by surface, electrode adhesion and cleanliness of skin | Current-controlled output, eliminating output variability. |
| USABILITY | Minimization of cables, low profile, and small size | Surface stimulators typically worn on the waist due to their large size (typical dimensions of 6 cm × 10 cm × 2.5 cm), requiring cables connecting the stimulator to the electrodes on the skin. Cables interfere with daily activities and restrict movement. | Elimination of cable connecting anode. Minimization of cable connecting cathode by placing system on skin near lead site. Preferably sized approx. 3.6 cm × 5.8 cm × 0.8 cm and 24 g. |
|  | Ease of recharging and low maintenance | Patients must open the battery compartment of surface stimulators and replace the battery regularly. This can be difficult for patients with impairments. Surface electrodes must be placed by skilled personnel daily. | Recharged by placing it on a recharging pad, an action that can he done with one hand. Percutaneous lead is placed once. |

Previous and ongoing studies suggest that PNS can significantly reduce post-amputation pain, but a system capable of delivering minimally invasive therapy safely and effectively does not exist. Systems and methods according to the present invention provide an innovative PNS system that addresses deficiencies in presently available devices in addition to introducing features that will improve the experience for the patient and clinician. Such systems and methods will improve clinical practice for pain management by providing clinicians with a therapy that can significantly reduce pain following amputation and improve QOL during the first 6 months of recovery without systemic side-effects or invasive procedures. For many amputees, pain subsides over time and the systems and methods according to the present invention may be the only pain therapy necessary. For patients who continue to experience pain, either the therapy can be re-dosed or a fully implantable electrical stimulation system can be considered.

Preferred technical features of a system according to the present invention include preferred stimulation parameters, electrical safety (including reduction of moisture ingress), physical characteristics, and operational functionality. Regarding stimulation parameters, a preferred stimulation amplitude is in a preferred range of about 0-30 milliamps, and more preferably in a preferred range of 0.1 mA-20 mA, +/−7%. A preferred pulse duration is about 0-500 microseconds, and more preferably is a range of 10-300 microseconds, +/−2-30%, but more preferably +/−2%. The pulse duration is preferably adjustable in increments of a single microsecond, though a coarser adjustment such as 10's of microseconds may be provided. A preferred stimulation frequency is in the range of about 0-500 Hz, and more preferably in a range of 1-200 Hz, +/−1-30%, but more preferably +/−1%.

Preferred electrical safety features include single-fault condition safety conditions that are generally standard to neurostimulation systems, but may also include improved, reduced moisture ingress resistance, which allows the external stimulator to be worn at all times, even during a shower, for example, and yet remain safe and reliable.

Preferred physical characteristics include relatively small size and mass for an external electrical stimulator. Preferred dimensions of the stimulator housing are about 3.6 centimeters×about 5.8 centimeters×about 0.8 centimeters. A preferred mass is about 24 grams.

Regarding operational functionality, an external stimulator according to the present invention is preferably controllable and/or programmable via a wireless interface that may be a radio interface, such as a Bluetooth interface or other RF interface, or an infrared communications interface. Whatever wireless protocol is selected, it is preferred that, upon command to transmit a control signal to the stimulator, such as from a controller manipulated by a patient or clinician, the action may be performed by the stimulator within one second. Wireless programmability and/or control allows for stimulator miniaturization. Stimulator miniaturization allows a low profile housing to enable a user to carry on and perform daily activities with limited concern of interfering with therapy provided by the stimulator, and further allows the user to keep the stimulator out of view, such as under clothing. Also regarding operational functionality, preferred stimulators according to the present invention have an operating life of at least one week at maximum settings used for RLP and PLP with stimulation settings at 5 mA amplitude, 20 microsecond pulse width and 100 Hz frequency. Such preferred operational functionality provides a user with at least one week without the need to recharge or replace a power source of the stimulator. Additionally, as already mentioned an operationally complete battery charge is preferred to occur in less than or equal to two hours of time.

Optimal stimulation of peripheral nerves for pain relief using percutaneous leads is most efficient through the generation and use of a controlled current, biphasic stimulus output with no net direct current (DC) and accurate stimulus parameters with precise programming. This may be accomplished through the use of circuit topologies and components capable of the required precision and stability despite changes in battery voltage, operating temperature, and aging. These requirements are easily achieved with conventional instrumentation design methods; however, these design methods are often at conflict with miniaturization and minimal power consumption (i.e., maximum battery life), which are both key features of a comfortable and easy to maintain external stimulator. To overcome this issue, precision circuit components and topologies may be used to ensure that the required accuracy and precision are achieved. Also, multiple power reduction methods may be used, such as disabling the portions of stimulation circuitry responsible for controlling the stimulus current between stimulus pulses, specifying fast turn-on voltage reference semiconductors, enabling them only shortly before use, and disabling them as soon as their measuring or output function is completed. These power minimization features may be implemented in the embedded software of the stimulator (i.e., in firmware of a microcontroller of the circuit board assembly).

Regarding an aspect of electrical safety, the electrical stimulation circuitry in the external stimulator preferably monitors total current drawn from the stimulus power supply. An excessive load, indicated by a high current draw, on this power supply may be caused by a component failure or a failure of the enclosure to isolate the circuitry from moisture and hazard currents through the compromised enclosure. When a high current or an excessive load is detected, the stimulator and/or power supply are shutdown, preferably within 100 milliseconds, and more preferably within 50 ms, confirming appropriate failsafe response.

Also related to electrical safety, and general reliability, is moisture ingress protection. It is preferable to ensure that the stimulator circuitry not damaged or made unsafe by moisture ingress. The technical challenges of packaging electronics for reliable operation in moist environments have been solved in numerous scientific, military, industrial and commercial applications, but the additional requirements of minimizing size and weight increase the technical burden. To achieve a safe reliable stimulator in a potentially moist environment, it is preferable to 1) eliminate or substantially reduce unnecessary seams in the molded plastic enclosure (e.g., switches, displays, battery access panel); 2) use sealed electrical connectors for the two-channel percutaneous lead receptacle and the snap connectors to the surface return electrode; and 3) provide a mechanism to allow venting the enclosure without providing a path for the ingress of fluids. A preferred stimulator housing is capable of preventing the ingress of water when sprayed from any direction at the housing for 10 minutes with specified flow rates and pressure. Note that the electrical safety function provided by the enclosure is single fault tolerant given the fail-safe stimulation power supply circuitry described above. Additional moisture control mechanisms may be employed such as conformal coating the circuit board and/or using a moisture getter (desiccant) inside the stimulator housing.

Figure 12:
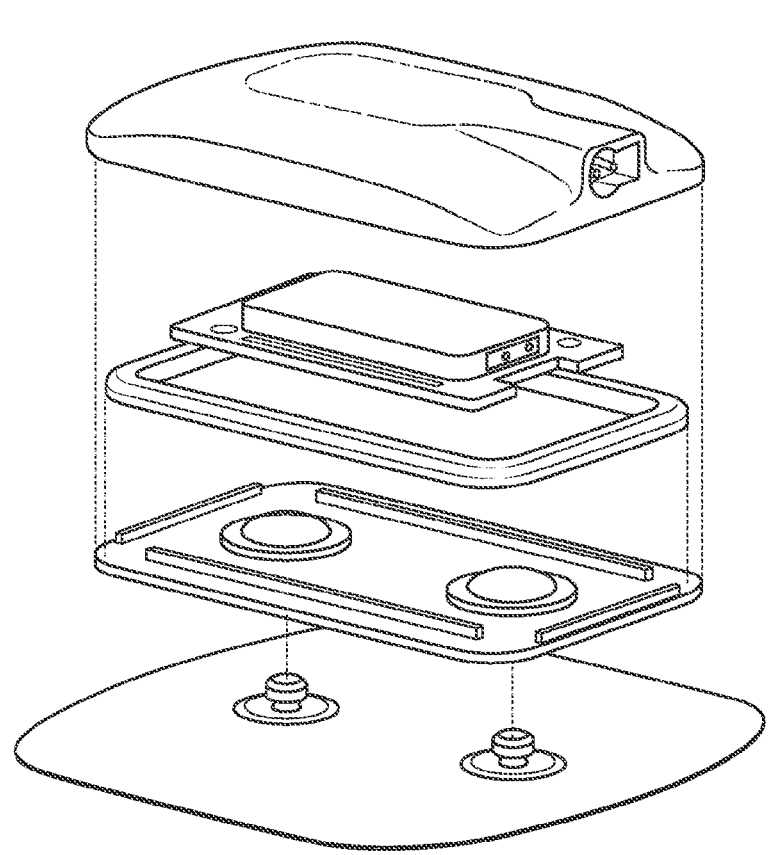
FIG. 12 shows a partial assembly view of an external stimulator and mounting patch according to the present invention.
Figure 13:
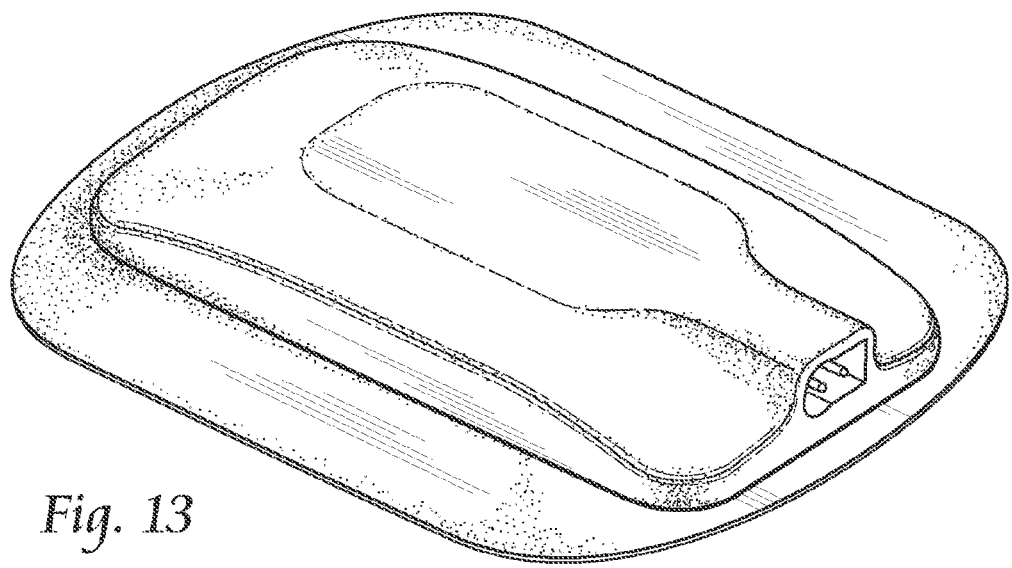
FIGS. 13-19 depict the stimulator from FIGS. 1-7 coupled to the mounting patch from FIGS. 8-11, including the mechanical and/or electrical engagement of the snap receptacles provided on the stimulator with the snaps provided on the mounting patch.
Figure 14:
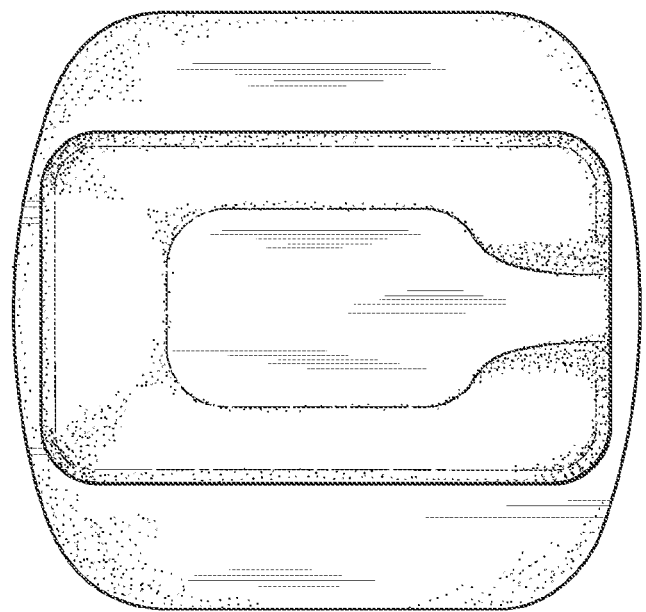
Figure 15:
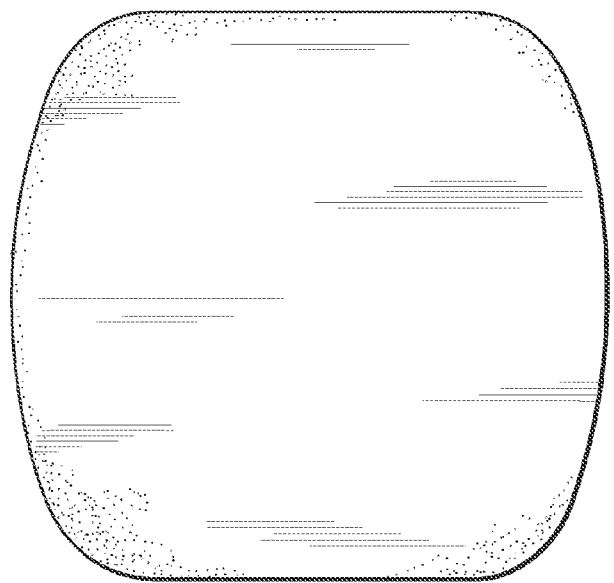
Figure 16:
Figure 17:
Figure 18:
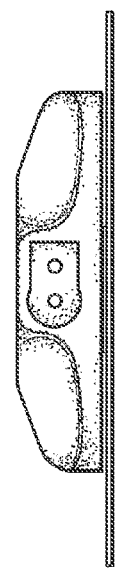
Figure 19:
Figure 20:
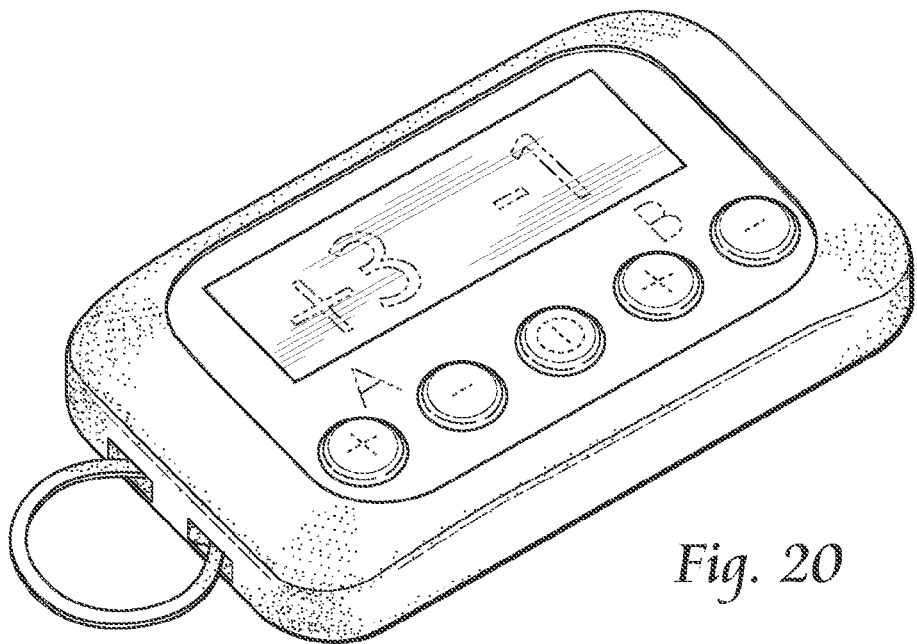
FIG. 20 depicts a first stimulator controller according to the present invention, which may be used by a patient or clinician to preferably wirelessly program and/or control the stimulator of FIGS. 1-7 before or after the stimulator is supported on a patient, such as by the mounting patch of FIGS. 8-11.
Figure 21:
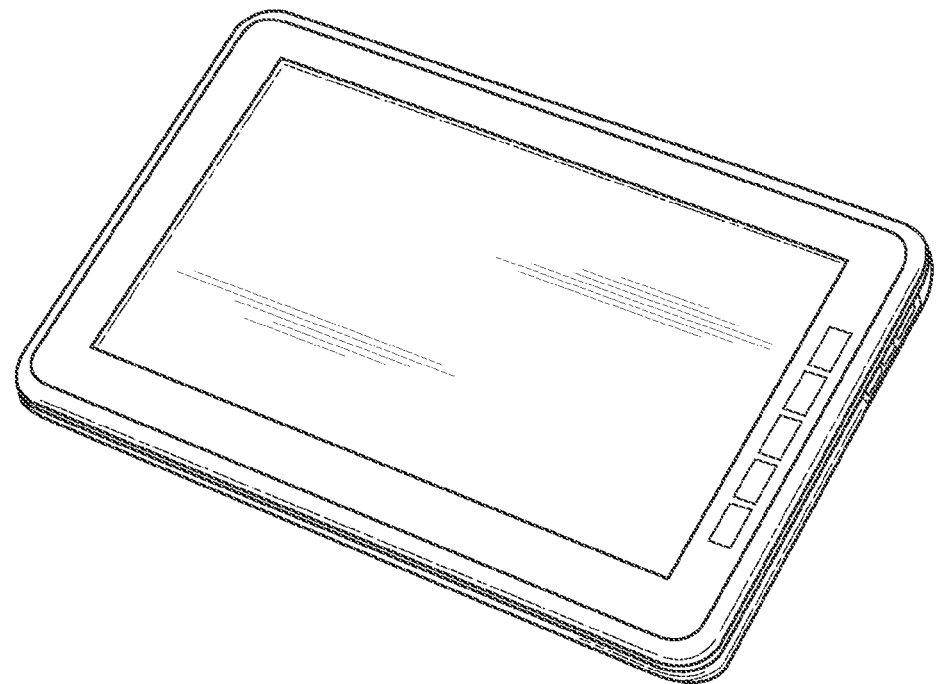
FIG. 21 depicts a second stimulator controller according to the present invention, which may be used by a patient or clinician to preferably wirelessly program and/or control the stimulator of FIGS. 1-7 before or after the stimulator is supported on a patient, such as by the mounting patch of FIGS. 8-11.
Figure 22:
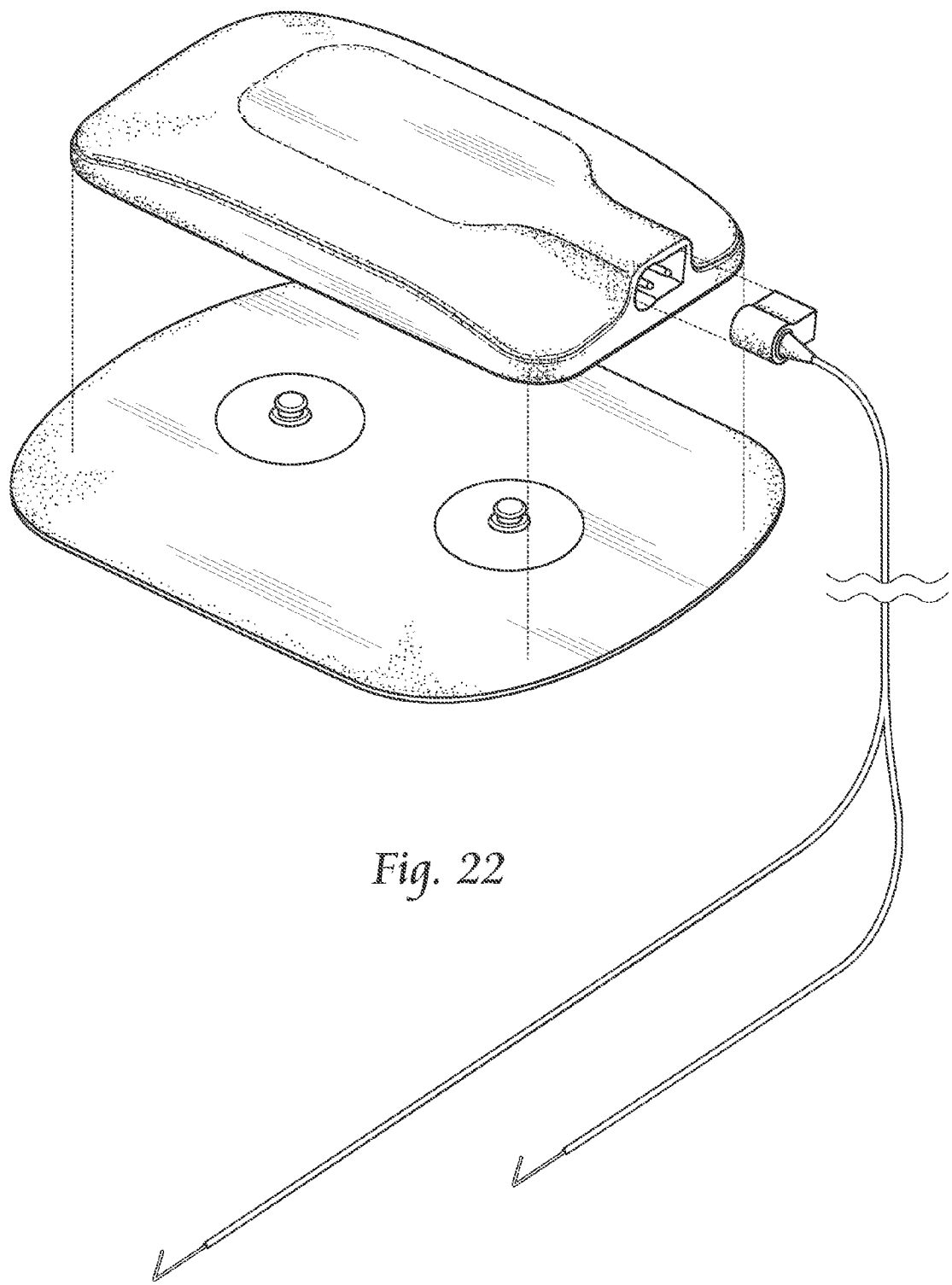
FIG. 22 is a partial assembly view including an external stimulator, mounting patch, and stimulating lead according to the present invention. The stimulating lead may have one or more stimulating electrodes supported thereby.
Figure 23:
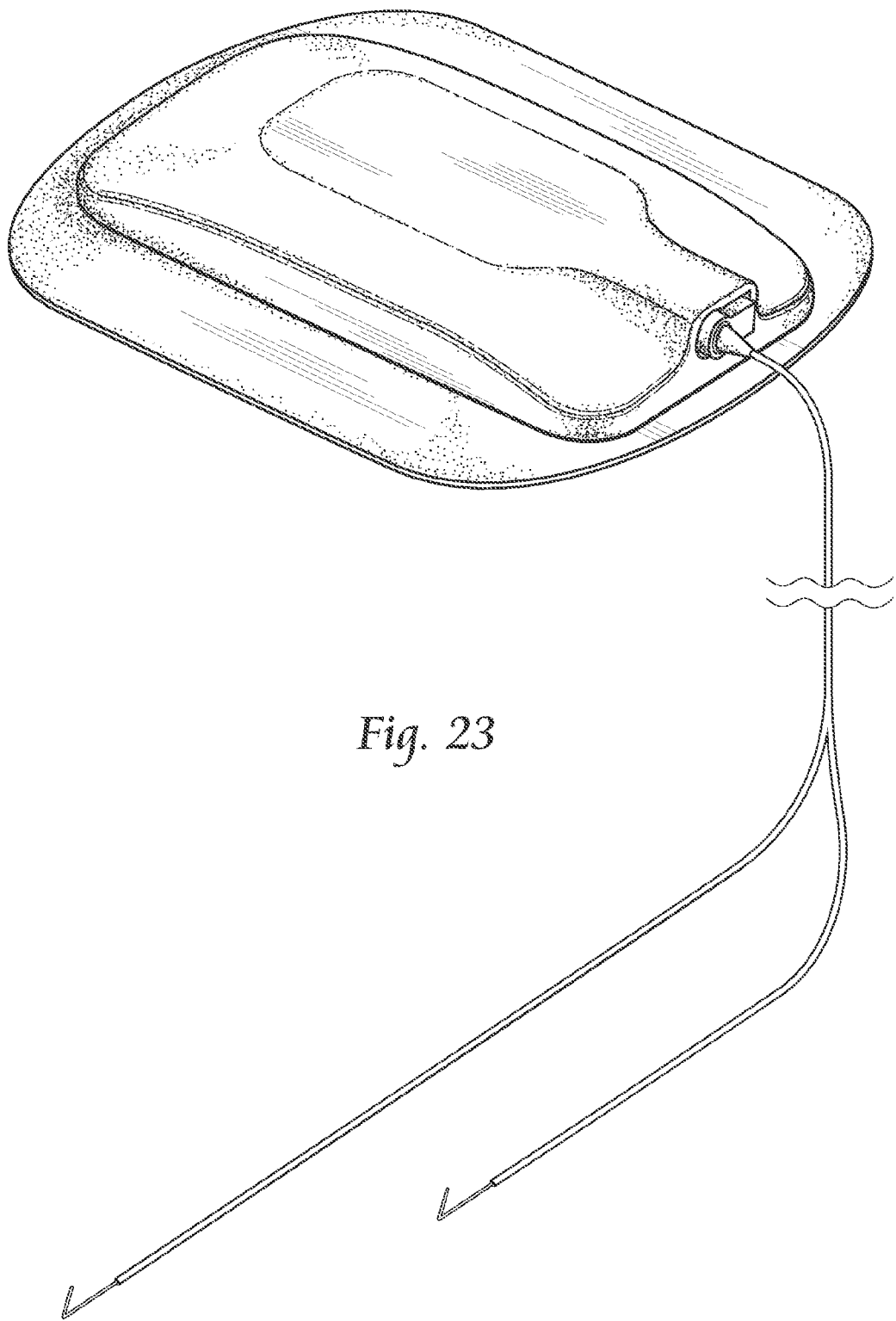
FIG. 23 is an assembled view of the embodiment of FIG. 22.
Figure 24:
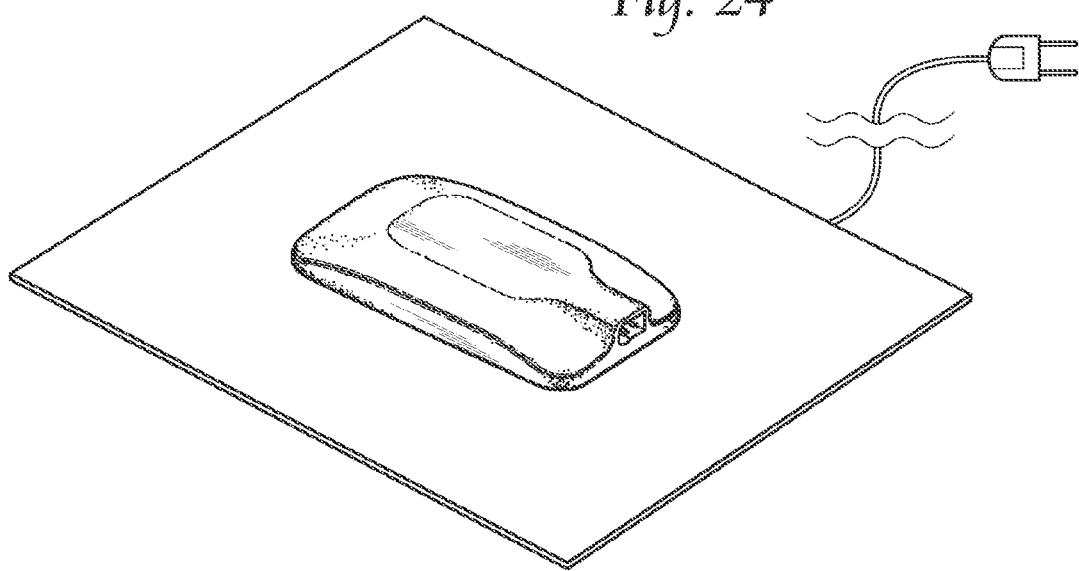
FIG. 24 is a perspective view of the stimulator of FIGS. 1-7 resting on an inductive charging mat, which is preferably connected to a power mains.

Patient comfort may be optimized by a stimulator and/or controller that are as small and light as possible. The stimulator preferably is approximately 3.6×5.8×0.8 cm and about 24 g. One way that such size may be achieved is by employing a button-less stimulator. Rather than having controls on the stimulator, a key-fob like controller containing a display and controls may be used by a patient or clinician to operate and/or program the stimulator, eliminating the size and weight associated with these elements (and increasing its integrity against moisture ingress). Lustran 348 ABS plastic is an exemplary material for the stimulator housing material for an optimal strength to weight ratio, durability and impact resistance, ease of fabrication, and evidence of biocompatibility. Internal rib structures may be incorporated into the device top housing to position and support the rechargeable lithium ion battery, circuit assembly, and recharging coil. The housing preferably has a smooth surface that is tapered at the periphery to minimize the potential for snagging. The top and bottom housing are preferably joined using an ultrasonic welding operation in order to ensure protection against water ingress, which may have the added features of eliminating the presence of thru-holes or lock-tabs frequently used for assembly of plastic housings of prior external stimulators. The size of the circuit assembly is preferably minimized through high-density circuit design and fabrication methods. FIG. 12 shows the internal construction of the stimulator, adapted to fit within a preferred target stimulator size.

Regarding control and/or programmability of the external stimulator, the use of a limited range wireless personal area network (PAN) communications system may be used to the utility of the stimulator because it eliminates the need for the patient to access the stimulator to start, stop, or adjust the intensity of the stimulation. The patient uses a small (i.e., 5.2×3.0×0.8 cm) wireless controller to control the stimulator and retrieve information from the stimulator (e.g., battery charge status, stimulus intensity). The clinician controller, such as a tablet PC, also uses the wireless link to retrieve usage information and to program stimulus settings. Driven by the rapid growth of short range wireless PANs in personal devices (e.g., cell phone head sets, remote controls for televisions, personal fitness and health monitoring devices), a number of micro-power wireless radio chip sets (i.e., integrated circuits specifically designed for short range communications at very low power levels) have become available with software for several low power communications protocols. Various chip sets and/or protocols may be used to implement a wireless telemetry link. The use of readily available chip sets and reference designs may significantly reduce the design effort required and the associated technology risks and ensure a ready source of low cost integrated circuits. Preferred are parameters such as performance levels (communications range (1 m in front of patient with stimulator anywhere on patient), interference recovery (using the standard test methods and limits of the protocol selected), peak and average current consumption (consistent with the selected battery capacity and operating life), and message quality and latency time (i.e., preferably at least 95% of all patient initiated commands axe received and acted on by the stimulator within 1 second).

Using a computer model of stimulator battery current consumption, the battery capacity was estimated for the stimulation circuitry to operate at the maximum optimal levels used to date during clinical trial investigations of peripheral nerve stimulation for post-amputation pain (5 mA, 20 μsec, and 100 Hz on each of the two stimulation channels). With a battery capacity of 100 mA-hours, the stimulator preferably has no need to be recharged more than once every eight days or so. The rechargeable battery may be formed from one or more Lithium Ion Polymer cells, preferably each that has 120 mA-hr or more of capacity, meet the package constraints, and preferably uses less than 25% of the available package volume. A commercially available charging pad compliant with the Wireless Power Consortium standard such as the Energizer® Inductive Charger may be used.

Preferably, the external stimulator with adhesive patch may be comfortable to wear on the body for 24 hours/day. The adhesive patch preferably adheres securely to a skin surface of a human body for at least 24 hours.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. A system comprising:
    a patch member having an adhesive disposed on a first side and a patch mounting structure disposed on a second side, opposite the first side, and an electrically conductive return electrode material disposed between the first side and the second side;
    an electrical stimulation device comprising:
        a housing having oppositely disposed, substantially planar top and bottom surfaces, wherein the top surface is imperforate;
        a device mounting structure on the bottom surface physically mated with the patch mounting structure;
        electrical stimulation generation circuitry disposed at least partially within the housing;
        one or more of a rechargeable battery, an inductive charging circuit adapted to receive an inductive charging signal, and a wireless communication module adapted to receive wireless communications to select or a stimulation pattern to be generated by the electrical stimulation circuitry;
    an-electrode electrically coupled to the electrical stimulation generation circuitry and configured to be percutenously inserted into a patient.

2. A system according to claim 1, wherein the top surface and the bottom surface of the housing are separated by a device thickness, wherein the housing further comprises a perimeter edge extending from the bottom surface and a sloped interface edge connecting the top surface to the perimeter edge along a majority of the perimeter thereof wherein the height of the perimeter edge, measured perpendicular to the top and bottom surfaces, is less than the device thickness.

3. A method of treating bodily pain of an animal comprising the steps of:
    providing a patch member having an adhesive disposed on a first side and a patch mounting structure disposed on a second side, opposite the first side, and an electrically conductive return electrode material disposed between the first side and the second side;
    providing an electrical stimulation device comprising:
        a housing having oppositely disposed, substantially planar top and bottom surfaces, wherein the top surface is imperforate;
        a device mounting structure on the bottom surface configured to physically mate with the patch mounting structure;
        electrical stimulation generation circuitry disposed at least partially within the housing;
        one or more of a rechargeable battery, an inductive charging circuit adapted to receive an inductive charging signal, and a wireless communication module adapted to receive wireless communications to select a stimulation pattern to be generated by the electrical stimulation circuitry;
    coupling the electrical stimulation device to the mounting structure;
    adhering the patch member to a skin surface of the animal;
    implanting an electrode in subcutaneous bodily tissue of the animal;
    electrically coupling the electrode to the electrical stimulation generation circuitry;
    generating electrical stimulation using the electrical stimulation generation circuitry;
    delivering the electrical stimulation to the bodily tissue;
    observing whether the electrical stimulation at least partially relieved the bodily pain.

4. A method according to claim 3, wherein the bodily pain is bodily pain existing in the body of the patient after an amputation of a body part.

5. A method according to claim 4, wherein the bodily pain did not exist prior to the amputation.

6. A method according to claim 5, wherein the bodily pain existed prior to the amputation, but was absent prior to trauma inflicted upon the body part.

7. A method according to claim 3, wherein implanting the electrode comprises percutaneously inserting the electrode into a patient body.

* * * * *